United States Patent
Sorebo et al.

(10) Patent No.: US 7,014,083 B2
(45) Date of Patent: Mar. 21, 2006

(54) SYSTEM AND METHOD FOR CONTROLLING THE WIDTH OF WEB MATERIAL

(75) Inventors: John Sorebo, Appleton, WI (US); Gregory J. Rajala, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 363 days.

(21) Appl. No.: 10/273,398

(22) Filed: Oct. 17, 2002

(65) Prior Publication Data

US 2004/0074942 A1 Apr. 22, 2004

(51) Int. Cl.
*B65H 20/30* (2006.01)
*G11B 15/56* (2006.01)

(52) U.S. Cl. .......................... 226/118.2; 226/45; 226/4; 226/16

(58) Field of Classification Search .............. 226/118.2, 226/45, 4, 16, 22, 20, 34
See application file for complete search history.

(56) References Cited

U.S. PATENT DOCUMENTS

| | | | |
|---|---|---|---|
| 2,796,965 A | | 6/1957 | Lamoureux |
| 4,381,586 A | | 5/1983 | Abler |
| 4,485,982 A | | 12/1984 | St. John et al. |
| 4,860,964 A | * | 8/1989 | Ishii et al. ............... 242/534.1 |
| 4,899,061 A | | 2/1990 | Van Hoek et al. |
| 4,920,621 A | | 5/1990 | Metzen |
| 5,271,284 A | | 12/1993 | Still et al. |
| 5,305,099 A | | 4/1994 | Morcos |
| 5,325,178 A | | 6/1994 | Louis et al. |
| 5,505,129 A | * | 4/1996 | Greb et al. ................. 101/219 |
| 5,554,262 A | | 9/1996 | Turner |
| 5,602,747 A | | 2/1997 | Rajala |
| 5,659,229 A | | 8/1997 | Rajala |
| 5,825,374 A | * | 10/1998 | Albertalli et al. ........... 346/136 |
| 6,314,333 B1 | | 11/2001 | Rajala et al. |
| 6,547,707 B1 | | 4/2003 | Cote |
| 6,652,686 B1 | * | 11/2003 | Coenen et al. ................ 156/64 |

OTHER PUBLICATIONS

Rajala, "Controlling Web Tension With a Dancer," Active Dancer Control For Web Handling Machines, Master's Thesis, University of Wisconson–Madison, 1995, Chapter 3, pp. 25–43.

* cited by examiner

*Primary Examiner*—Eileen D. Lillis
*Assistant Examiner*—Evan H Langdon
(74) *Attorney, Agent, or Firm*—Senniger Powers

(57) ABSTRACT

A system and method for controlling the width of a web material supplied to a machine by adjusting the tension of the web material. An operator defines a target web width via an input device. The input device generates a reference signal representative of the target web width. A sensing device senses the width of the web material supplied to the machine and generate feedback signal representative of the sensed width. A control circuit compares the feedback and reference signals and generates a tensioning signal as a function of the comparison. A tensioning device is responsive to tensioning signal for adjusting web tension.

24 Claims, 7 Drawing Sheets

SYSTEM AND METHOD FOR CONTROLLING THE WIDTH OF WEB MATERIAL

FIELD OF THE INVENTION

The invention relates to a system and method for controlling the width of a web by adjusting its tension. In particular, the invention relates to a system and method for maintaining the width of a web fed to an absorbent garment manufacturing machine.

BACKGROUND OF THE INVENTION

Articles such as disposable absorbent garments have numerous application including diapers, training pants, feminine care products, and adult incontinence products. A typical disposable absorbent garment is formed as a composite structure including an absorbent assembly disposed between a liquid permeable bodyside liner and a liquid impermeable outer cover. These components can be combined with other materials and features such as elastic materials and containment structures to form a product which is specifically suited to its intended purposes.

For example, one such garment is a child's diaper, which has a central absorbent chassis and front and back side panels extending laterally out from the chassis adjacent longitudinally opposite ends thereof. A portion of each of the front and back side panels has a respective fastening component disposed thereon. During manufacture of the diaper, the central absorbent chassis is initially formed generally flat and then folded over so that the front and back side panels face each other. The respective fastening components of the front and back side panels are then aligned and connected together to define an engagement seam. Upon securing the front and back side panel fastening components together, the pre-fastened diaper is in its fully assembled three-dimensional form having an interior space bounded in part by the engagement seam.

Absorbent garments may be formed from a woven web material or a non-woven web material. A non-woven web is a web having a structure of individual fibers or threads which are interlaid, but not in a regular or identifiable manner as in a knitted or woven fabric. The term also includes individual filaments and strands, yarns or tows as well as foams and films that have been fibrillated, apertured, or otherwise treated to impart fabric-like properties. Non-woven fabrics or webs have been formed from many processes such as for example, meltblowing processes, spunbonding processes, and bonded carded web processes.

The failure to properly control woven or non-woven fabrics supplied to a manufacturing process can result in quality concerns, additional material costs, and defective products. In order to avoid defects when forming diapers from web material, it is important that the web width be controlled during the manufacturing process. The importance of web width control becomes apparent when other components (e.g., ears) must be tacked onto a sausage of the non-woven web material. Defective absorbent garments can result from improper width alignment of the sausage components. One method of controlling web width involves monitoring and controlling web tension during manufacturing. However, this method often proves inadequate in controlling width variability. As a result, diaper manufacturing tolerances are widening.

In spite of past efforts, there is a need for improved methods and systems for controlling web width variability during a manufacturing process. There is a need for systems and methods that permit monitoring and controlling web width during manufacturing.

The invention described below addresses one or more of these and other disadvantages and needs.

SUMMARY OF THE INVENTION

In accordance with one aspect of the invention, a system is provided for controlling a web material traveling along a path. The system includes an input device that is responsive to operator information for indicating a target width range for the web material. A width sensor senses a width of the web material. A tensioning device controls the tension of the web material in response to a tensioning signal. A control circuit responsive to the input device and responsive to the width sensor provides the tensioning signal to the tensioning device to maintain the width of the web within the target width range as indicated by the input device.

In accordance with another aspect of the invention, a system is provided for controlling a web material traveling along a path. A user station responsive to operator information generates a reference signal that indicates a target width range for the web material. A width sensor senses a width of the web material and generates a feedback signal. A tensioning device adjusts a tension of the web material in response to a tensioning signal. A controller is linked to the user station and to the width sensor for receiving the reference signal and the feedback signal. The controller generates the tensioning signal as a function of the difference between the received reference signal and received feedback signal, and the generated tensioning signal is provided to the tensioning device to adjust the tension of the web material.

In accordance with yet another aspect of the invention, a method is provided for controlling a tension of a web material. The method first includes defining a target web width range for the web material. The method further includes sensing a width of the web material. The method further includes comparing the sensed width with the target width. The method further includes increasing the tension of the web when the sensed width is greater than the target width range, and decreasing the tension of the web when the sensed width is less than the target width range.

Alternatively the invention may comprise various other methods and systems. Other objects and advantages will become apparent to those skilled in the art from the detailed description herein read in conjunction with the attached drawings.

BRIEF DESCRIPTION OF DRAWINGS

Corresponding reference characters indicate corresponding parts throughout the drawings.

DETAILED DESCRIPTION

Figure 1:
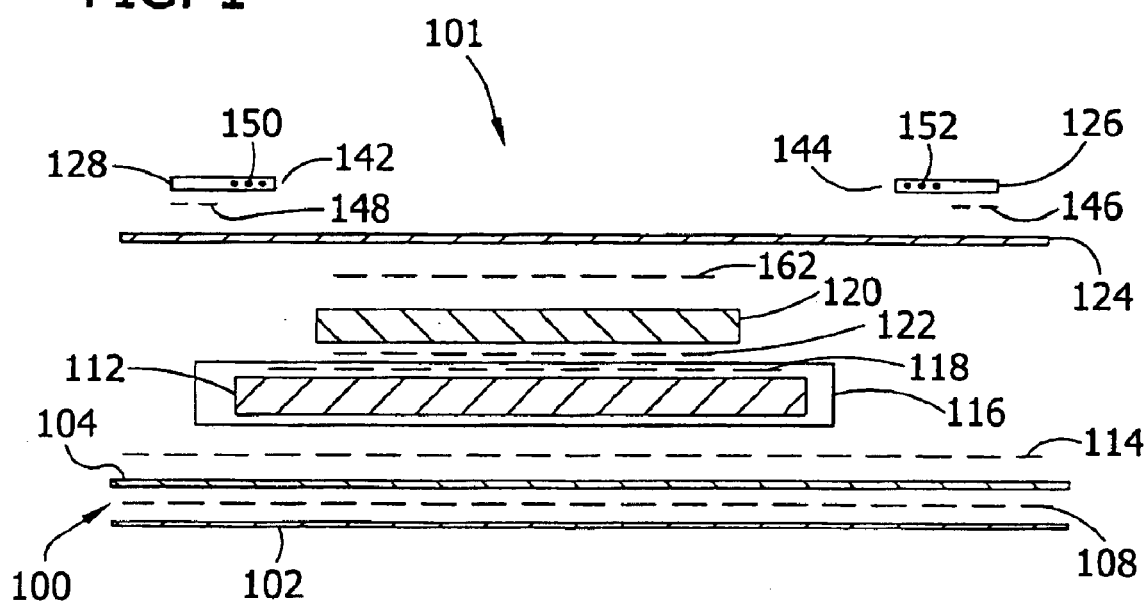
FIG. 1 is a cross sectional view of a diaper taken across line 8-8 of FIG. 3.
Figure 3:
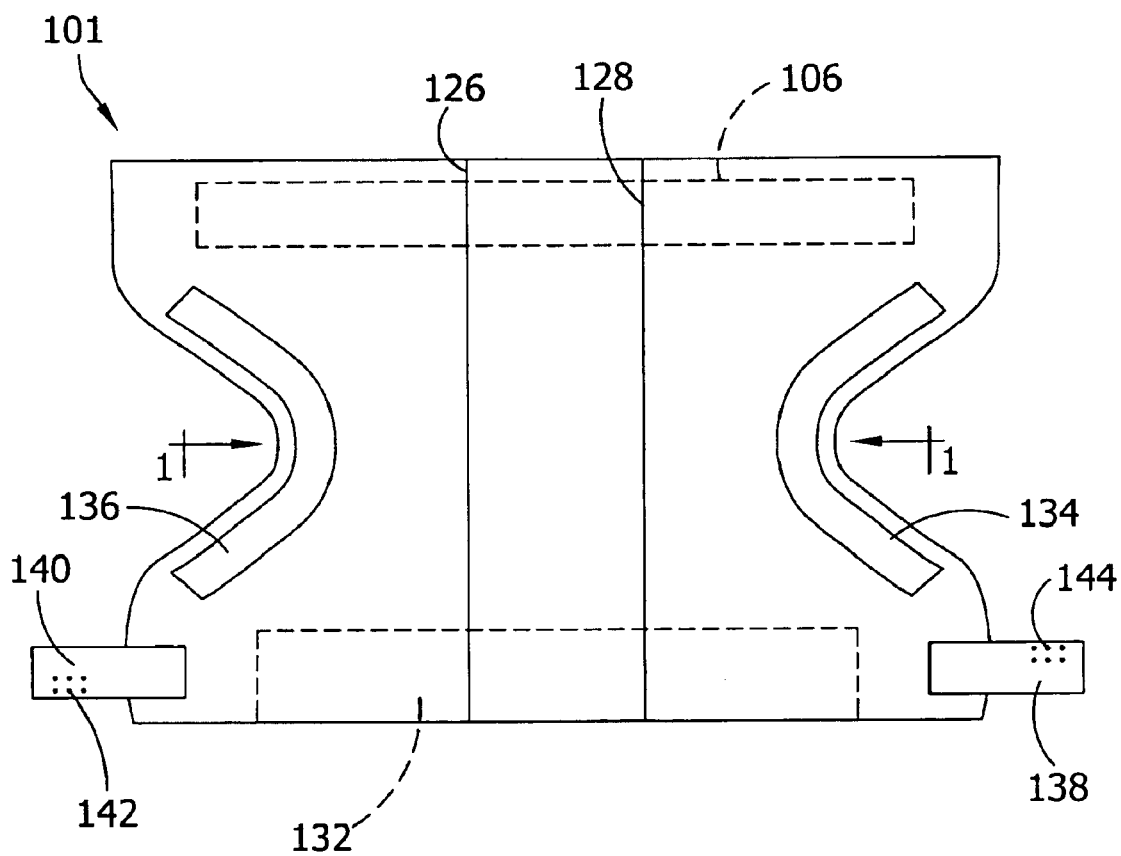
FIG. 3 is a top view of a diaper.

Referring now to FIG. 1, there is shown a cross-section of a diaper 101 along the line 8-8 of FIG. 3, which comprises generally an outer cover 100 which comprises an outer layer 102 and an inner layer 104. The outer cover 100 is desirably stretchable and may or may not be somewhat elastic. As used herein, the term "stretchable" refers to a material that may be extensible and/or elastic. That is, the material may be extended, deformed or the like, without breaking, and may or may not significantly retract after removal of an extending force. As used herein, the term "elastic" refers to that property of a material where upon removal of an elongating force, the material is capable of substantially recovering its original size and shape or the material exhibits a significant retractive force. More desirably, the outer cover 100 is extensible such that once stretched under the weight of an insulted absorbent body, the outer cover will not retract substantially back toward its original position. As used herein, the term "extensible" refers to that property of a material where upon removal of an elongating force, the material experiences a substantially permanent deformation or the material does not exhibit a significant retractive force. For example, the outer cover 100 may be stretched approximately 25% to 150% beyond its original length with a relatively low force required to extend. More desirably, the outer cover 100 may be stretched approximately 50% to 100% beyond its original length and most desirably about 50% beyond its original length under a low stretching force. As a further example, in one embodiment a 25% elongation is achieved upon application of a force of in the range of about 30 g/in to about 200 g/in, more desirably between about 70 g/in and 150 g/in and most desirably about 100 g/in. It is also contemplated that the outer cover 100 may instead be generally non-extensible and remain within the scope of this invention The outer cover 100 can also be desirably constructed to support a selected hydrohead of water substantially without leakage therethrough. A suitable technique for determining the resistance of a material to liquid penetration is Federal Test Method Standard FTMS 191 Method 5514, 1978, or an equivalent thereof Since the outer cover 100 can be extensible, a layer of nylon net material having a thickness of about 0.1 mm may be needed to support the outer cover material for this test. The net material may be provided by nylon threads arranged in a hexagonal or honeycomb-like pattern with openings approximately 4 mm across. For example, the net material may be purchased from Wal-Mart Stores under the trade designation T-246. The net material is liquid pervious and does not significantly affect the hydrohead values obtained. The extensible outer cover 100 is desirably sufficiently impermeable to liquid and semi-liquid materials to substantially prevent the undesired leakage of waste materials, such as urine and feces. For example, the extensible outer cover 100 can desirably support a hydrohead of at least about 45 centimeters (cm) substantially without leakage. The extensible outer cover 100 can alternatively support a hydrohead of at least about 55 cm, and optionally, can support a hydrohead of at least about 60 cm, or more, to provide improved benefits.

The extensible outer cover 100 can be composed of various materials which provide the desired properties set forth herein. For example, the extensible outer cover 100 is desirably composed of a neckable or otherwise necked fabric, but may instead, or may additionally, be composed of a creped fabric, a crimped fiber fabric, an extendable fiber fabric, a bonded-carded fabric, a micro-pleated fabric, polymer films or the like. The fabrics may be woven or non-woven materials, such as spunbond fabrics.

As used herein, the term "neck" or "neck stretch" interchangeably means that a material is drawn such that it is extended under conditions reducing its width or its transverse dimension by drawing and elongating to increase the length of the fabric. The controlled drawing may take place under cool temperatures, room temperature or greater temperatures and is limited to an increase in overall dimension in the direction being drawn up to the elongation required to break the fabric. The necking process typically involves unwinding a sheet from a supply roll and passing it through a brake nip roll assembly driven at a given linear speed. A take-up roll or nip, operating at a linear speed higher than the brake nip roll, draws the fabric and generates the tension needed to elongate and neck the fabric. U.S. Pat. No. 4,965,122 entitled REVERSIBLY NECKED MATERIAL, by M. T. Morman which issued Oct. 23, 1990, the entire disclosure of which is hereby incorporated by reference in a manner consistent with the present document, discloses a process for providing a reversibly necked non-woven material which may include necking the material, then heating the necked material, followed by cooling.

As used herein, the term "neckable material or layer" means any material which can be necked such as a nonwoven, woven, or knitted material. The term "necked material" refers to any material which has been drawn in at least one dimension, (e.g. lengthwise), reducing the transverse dimension, (e.g. width), such that when the drawing force is removed, the material can be pulled back to its original width. The necked material typically has a higher basis weight per unit area than the un-necked material. When the necked material is pulled back to its original un-necked width, it should have about the same basis weight as the un-necked material. This differs from stretching/orienting a material layer, during which the layer is thinned and the basis weight is permanently reduced.

Typically, such necked nonwoven fabric materials are capable of being necked up to about 80 percent. For example, the extensible outer cover 100 may be composed of a material which has been necked from about 10 to about 80 percent, desirably from about 20 to about 60 percent, and more desirably from about 30 to about 50 percent for improved performance. For the purposes of the present disclosure, the term "percent necked" or "percent neck-down" refers to a ratio or percentage determined by measuring the difference between the pre-necked dimension and the necked dimension of a neckable material, and then dividing that difference by the pre-necked dimension of the neckable material and multiplying by 100 for percentage. The percent necked can be determined in accordance with the description in the above-mentioned U.S. Pat. No. 4,965,122.

The outer cover 100 is desirably a multi-layered laminate structure, and more desirably a necked, multi-layer laminate structure, to provide the desired levels of extensibility as well as liquid impermeability and vapor permeability. For example, the outer cover 100 of the illustrated embodiment is of two-layer construction, including an outer layer 102 constructed of a vapor and liquid permeable necked material and an inner layer 104 constructed of a liquid impermeable material, with the two layers being secured together by a suitable laminate adhesive 108, which as discussed further herein, can be the adhesive composition of the present invention. The outer cover may also be a single layer.

The liquid permeable outer layer 102 can be any suitable material as described above and is desirably one which provides a generally cloth-like texture. Suitable neckable materials for the outer layer 102 include non-woven webs, woven materials and knitted materials such as those described in the above-mentioned U.S. Pat. No. 4,965,122. Non-woven fabrics or webs have been formed from many processes, for example, bonded carded web processes, melt-blowing processes and spunbonding processes. The non-elastic neckable material is desirably formed from at least one member selected from fibers and filaments of inelastic polymers. Such polymers include polyesters, for example, polyethylene terephthalate, polyolefins, for example, polyethylene and polypropylene, polyamides, for example, nylon 6 and nylon 66. A preferred material for the outer layer 102 of outer cover 100 is a spunbond polypropylene. These fibers or filaments are used alone or in a mixture of two or more thereof. Suitable fibers for forming the neckable material include natural and synthetic fibers as well as bicomponent, multi-component, and shaped polymer fibers.

Many polyolefins are available for fiber production including, for example, fiber forming polypropylenes including Exxon Chemical Company's Escorene PD 3445 polypropylene and Himont Chemical Company's PF-304. Polyethylenes such as Dow Chemical's ASPUN 6811A linear low density polyethylene, 2553 LLDPE and 25355 and 12350 high density polyethylene are also suitable polymers. The nonwoven web layer may be bonded to impart a discrete bond pattern with a prescribed bond surface area If too much bond area is present on the neckable material, it will break before it necks. If there is not enough bond area, then the neckable material will pull apart. Typically, the percent bonding area useful in the present invention ranges from around 5 percent to around 40 percent of the area of the neckable material.

One particular example of suitable material from which the outer layer 102 may be constructed is a 0.4 osy (ounce per square yard) or 14 gsm (grams per square meter) spunbond polypropylene non-woven web which is neckable in the range of about 35% to 45%. Also, while it is not a necessity for the outer layer 102 of the outer cover 100 to be liquid permeable, it is desired that it have a cloth-like texture.

The liquid impermeable inner layer 104 of the outer cover 100 can be either vapor permeable (i.e., "breathable") or vapor impermeable. The inner layer 104 is desirably manufactured from a thin plastic film, such as a thin polypropylene film, although other flexible liquid impermeable materials may also be used. More particularly, the inner layer 104 can be made from either cast or blown film equipment, can be coextruded and can be embossed if so desired. It is understood that the inner layer 104 may otherwise be made from any suitable non-elastic polymer composition and may include multiple layers. Where the inner layer 104 is vapor permeable, it may contain such fillers as micropore developing fillers, e.g. calcium carbonate; opacifying agents, e.g. titanium dioxide; and antiblock additives, e.g. diatomaceous earth. Suitable polymers for the inner layer 104 include but are not limited to non-elastic extrudable polymers such as polyolefin or a blend of polyolefins, nylon, polyester and ethylene vinyl alcohol. More particularly, useful polyolefins include polypropylene and polyethylene. Other useful polymers include those described in U.S. Pat. No. 4,777,073 to Sheth, assigned to Exxon Chemical Patents Inc., such as a copolymer of polypropylene and low density polyethylene or linear low density polyethylene.

Alternative polymers for the inner layer 104 include those referred to as single site catalyzed polymers such as "metallocene" polymers produced according to a metallocene process and which have limited elastic properties. The term "metallocene-catalyzed polymers" as used herein includes those polymer materials that are produced by the polymerization of at least ethylene using metallocenes or constrained geometry catalysts, a class of organometallic complexes, as catalysts. For example, a common metallocene is ferrocene, a complex of a metal between two cyclopentadienyl (Cp) ligands. Such metallocene polymers are available from Exxon Chemical Company of Baytown, Tex. under the trade name EXXPOL® for polypropylene based polymers and EXACT® for polyethylene based polymers and from Dow Chemical Company of Midland, Mich. under the name ENGAGE®. Desirably, the metallocene polymers are selected from copolymers of ethylene and 1-butene, copolymers of ethylene and 1-hexene, copolymers of ethylene and 1-octene and combinations thereof.

The inner layer 104 may be laminated to the neckable material of the outer layer 102 to form the laminate outer cover 100 utilizing the adhesive compositions of the present invention or by conventional methods known in the art including adhesive bonding, point bonding, thermal point bonding, and sonic welding. The outer cover 100 is then necked by conventional necking processes which typically vary the surface speed of the web to draw or neck the laminate. Such necking provides striated rugosities in the film and/or laminate resulting in transverse extensibility and retractability to the necked laminate and more "cloth-like" aesthetics. It is known that stretching and orienting a filled film layer (e.g., inner layer 104) causes micropores to form in the film, but longitudinal striated rugosities do not typically form in the film layer when stretched. The film layer would instead become physically thinner and may narrow slightly. By necking the laminate, the non-elastic neckable material, which is attached to the nonelastic film layer, will neck and bring the non-elastic film layer with it, thereby forming the longitudinal striated rugosities in the film which allow the film layer to extend in the transverse direction.

Alternative necked laminate materials that could be used to provide the outer cover 100 with the desired extensibility and liquid impermeability are described in U.S. Pat. Application Ser. No. 09/460,490 filed Dec. 14, 1999 and entitled "BREATHABLE LAMINATE PERMANENTLY CONFORMABLE TO THE CONTOURS OF A WEARER", the entire disclosure of which is hereby incorporated by reference in a manner consistent with the present document. Other suitable necked laminates that include at least one non-elastic neckable material laminated to at least one non-elastic film material are described in U.S. Pat. Application Ser. No. 09/455,513 filed Dec. 6, 1999 and entitled "TRANSVERSELY EXTENSIBLE AND RETRACTABLE NECKED LAMINATE OF NON-ELASTIC SHEET LAYERS", the entire disclosure of which is hereby incorporated by reference consistent with the present document. However, it is to be understood that the laminate outer cover need not be composed of a neckable or necked material to be useful with the adhesive compositions of the present invention.

Referring now to FIG. 3, diaper 101 also includes a loop material or "pub patch" 106 adhesively bound to the outer cover for receiving hook material for fastening or closing the diaper during wear. The adhesive composition utilized to bond the pub patch to the outer cover may comprise the adhesive compositions of the present invention. The loop material may include a nonwoven fabric having continuous bonded areas defining a plurality of discrete unbonded areas. The fibers or filaments within the discrete unbonded areas of the fabric are dimensionally stabilized by the continuous bonded areas that encircle or surround each unbonded area, such that no support or backing layer of film or adhesive is required. The unbonded areas are specifically designed to afford spaces between fibers or filaments within the unbonded area that remain sufficiently open or large to receive and engage hook elements of the complementary hook material. In particular, a pattern-unbonded nonwoven fabric or web may include a spunbond nonwoven web formed of single component or multi-component melt-spun filaments. For example, the pub patch may be formed from a laminated structure including a polyethylene component and a polypropylene component adhesively bonded together and the polypropylene component is outwardly facing to accept a hook-type fastener.

At least one surface of the nonwoven fabric can include a plurality of discrete, unbonded areas surrounded or encircled by continuous bonded areas. The continuous bonded areas dimensionally stabilize the fibers or filaments forming the nonwoven web by bonding or fusing together the portions of the fibers or filaments that extend outside of the unbonded areas into the bonded areas, while leaving the fibers or filaments within the unbonded areas substantially free of bonding or fusing. The degree of bonding or fising within the bonding areas desirably is sufficient to render the nonwoven web non-fibrous within the bonded areas, leaving the fibers or filaments within the unbonded areas to act as "loops" for receiving and engaging hook elements. Examples of suitable point-unbonded fabrics are described in U.S. Pat. No. 5,858,515 entitled PATTERN-UNBONDED NONWOVEN WEB AND PROCESS FOR MAKING THE SAME, by T. J. Stokes et al., the entire disclosure of which is incorporated herein by reference in a manner consistent with the present document.

Referring again to FIG. 1, diaper 101 additionally comprises an absorbent core 112 which can be adhesively bonded to a tissue wrap 116 (also commonly referred to as a tissue wrap sheet) by adhesive 118 which can be the adhesive composition of the present invention. Alternatively, the absorbent core need not have a tissue wrap and can simply be sandwiched between the outer cover and the bodyside liner. Absorbent core 112 may have any of a number of shapes, including rectangular, I-shaped, or T-shaped and is desirably narrower in the crotch region than in the front or back regions of the diaper 101. The size and the absorbent capacity of absorbent core 112 will be selected according to the size of the intended wearer and the liquid loading imparted by the intended use of the diaper. Further, the size and the absorbent capacity of the absorbent core 112 can be varied to accommodate various sized wearers. In addition, it has been found that the densities and/or basis weights of the absorbent core 112 can be varied. In the embodiment described herein, the absorbent core 112 typically has an absorbent capacity of at least about 300 grams of synthetic urine.

The absorbent core 112 desirably includes hydrophilic fibers and superabsorbent particles, as described more fully below. Various types of wettable, hydrophilic fibrous material can be used to form the absorbent core 112. Examples of suitable fibers include naturally occurring organic fibers composed of intrinsically wettable material, such as cellulosic fibers; synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers; and synthetic fibers composed of a nonwettable thermoplastic polymer, such as polypropylene fibers, which have been hydrophilized by appropriate means. The fibers may be hydrophilized, for example, by treatment with silica, treatment with a material which has a suitable hydrophilic moiety and is not readily removable from the fiber, or by sheathing the nonwettable, hydrophobic fiber with a hydrophilic polymer during or after the formation of the fiber. For the purposes of the present invention, it is contemplated that selected blends of the various types of fibers mentioned above may also be employed.

The absorbent core 112 may include a combination of hydrophilic fibers and high-absorbency material. However, it is understood that absorbent bodies having absorbent layers of other compositions and having dimensions other than described may be used without departing from the scope of the present invention. More specifically, the high-absorbency material in absorbent core 112 can be selected from natural, synthetic, and modified natural polymers and materials. The high-absorbency materials can be inorganic materials, such as silica gels, or organic compounds, such as crosslinked polymers. The term "crosslinked" refers to methods for effectively rendering normally water-soluble materials substantially water insoluble but swellable. Such methods include, for example, physical entanglement, crystalline domains, covalent bonds, ionic complexes and associations, hydrophilic associations such as hydrogen bonding, and hydrophobic associations or Van der Waals forces.

Examples of synthetic, polymeric, high-absorbency materials include the alkali metal and ammonium salts of poly(acrylic acid) and poly(methacrylic acid), poly(acrylamides), poly(vinyl ethers), maleic anhydride copolymers with vinyl ethers and alpha-olefins, poly(vinyl pyrrolidone), poly(vinyl morpholinone), poly(vinyl alcohol), and mixtures and copolymers thereof. Further polymers suitable for use in absorbent core 112 include natural and modified natural polymers, such as hydrolyzed acryloritrilegrafted starch, acrylic acid grafted starch, methyl cellulose, carboxymethyl cellulose, hydroxypropyl cellulose, and the natural gums, such as alginates, xanthan gum, locust bean gum, and the like. Mixtures of natural and wholly or partially synthetic absorbent polymers can also be useful in the present invention.

The high absorbency material may be in any of a wide variety of geometric forms. As a general rule, it is preferred that the high absorbency material be in the form of discrete particles or beads. However, the high absorbency material may also be in the form of fibers, flakes, rods, spheres, needles, or the like. In general, the high absorbency material is present in the absorbent core 112 in an amount of from about 5 to about 90 percent by weight, desirably in an amount of at least about 30 percent by weight, and even more desirably in an amount of at least about 50 percent by weight based on a total weight of absorbent core 112.

An example of high-absorbency material suitable for use in the absorbent core 112 is SANWET IM 3900 polymer available from Hoechst Celanese, a business having offices in Portsmouth, Va. Other suitable superabsorbents may include FAVOR SXM 880 polymer obtained from Stockhausen, a business having offices in Greensboro, N.C.

As discussed above, absorbent core 112 can be wrapped in tissue wrap 116, and adhesively bonded thereto with adhesive 118, which may be the adhesive composition of the present invention. Tissue wrap 116 is a substantially hydrophilic tissue wrap employed to help maintain the integrity of the structure of absorbent core 112 and to stabilize absorbent core 112. Tissue wrap 116 can be made of an absorbent cellulosic material, such as creped wadding or a high wet-strength tissue. Tissue wrap 116 can be configured to provide a wicking layer that helps to rapidly distribute liquid over the mass of absorbent fibers constituting the absorbent core 112.

Tissue wrap 116 can be adhesively bonded to surge management layer 120 with adhesive 122, which may be the adhesive composition of the present invention. Surge management layer 120 is typically less hydrophilic than the absorbent core 112 and has an operable level of density and basis weight to quickly collect and temporarily hold liquid surges, to transport the liquid from its initial entrance point and to substantially completely release the liquid to the absorbent core. This configuration is intended to minimize the likelihood of the liquid pooling and collecting on the portion of the diaper against the wearer's skin, thereby reducing the feeling of wetness by the wearer. The structure of the surge management layer 120 also generally enhances the air exchange within the diaper 101.

Various woven and nonwoven fabrics can be used to construct the surge management layer 120. For example, the surge management layer 120 may be a layer made of a meltblown or spunbond web of synthetic fibers, such as polyolefin fibers. The surge management layer 120 may also be a bonded-carded-web or an airlaid web composed of natural and synthetic fibers. The bonded-carded-web may, for example, be a thermally bonded web that is bonded using low melt binder fibers, powder or adhesive. The webs can optionally include a mixture of different fibers. The surge management layer 120 may be composed of a substantially hydrophobic material, and the hydrophobic material may optionally be treated with a surfactant or otherwise processed to impart a desired level of wettability and hydrophilicity. As one example, the surge management layer 120 includes a hydrophobic, nonwoven material having a basis weight of from about 30 to about 120 grams per square meter.

The absorbent core 112 is typically positioned in liquid communication with the surge management layer 120 to receive liquids released from the surge management layer, and to hold and store the liquid. In the illustrated embodiment, the surge management layer 120 is a separate layer positioned over the absorbent core 112. The surge management layer 120 serves to quickly collect and temporarily hold discharged liquids, to transport such liquids from the point of initial contact and spread the liquid to other parts of the surge management layer 120, and then to substantially completely release such liquids into the absorbent core 112.

The surge management layer 120 can be of any desired shape. Suitable shapes include for example, circular, rectangular, triangular, trapezoidal, oblong, dog-boned, hourglass-shaped, or oval.

Additional materials suitable for the surge management layer 120 are set forth in U.S. Pat. No. 5,486,166 issued Jan. 23, 1996 in the name of C. Ellis et al. and entitled "FIBROUS NONWOVEN WEB SURGE LAYER FOR PERSONAL CARE ABSORBENT ARTICLES AND THE LIKE"; U.S. Pat. No. 5,490,846 issued Feb. 13, 1996 in the name of Ellis et al. and entitled "IMPROVED SURGE MANAGEMENT FIBROUS NONWOVEN WEB FOR PERSONAL CARE ABSORBENT ARTICLES AND THE LIKE"; and U.S. Pat. No. 5,364,382 issued Nov. 15, 1994 in the name of Latimer et al. and entitled "ABSORBENT STRUCTURE HAVING IMPROVED FLUID SURGE MANAGEMENT AND PRODUCT INCORPORATING SAME", the disclosures of which are hereby incorporated by reference in a manner consistent with the present document.

The surge management layer 120 is adhesively bonded to the bodyside liner 124 with adhesive 162. The adhesive 162 may be the adhesive composition of the present invention. The bodyside liner 124 is generally bonded to the inner layer 10 of outer cover 100 with adhesive 114 and is desirably pliable, soft feeling, and nonirritating to the wearer's skin, and is employed to help isolate the wearer's skin from the absorbent core 112. The bodyside liner 124 is less hydrophilic than the absorbent core 112, to present a relatively dry surface to the wearer, and is sufficiently porous to be liquid permeable, permitting liquid to readily penetrate through its thickness. A suitable bodyside liner 124 may be manufactured from a wide selection of web materials, but is desirably capable of stretching in at least one direction (e.g., longitudinal or lateral). Various woven and nonwoven fabrics including either or both synthetic and natural fibers can be used for the bodyside liner 124. For example, the bodyside liner 124 may be composed of a meltblown or spunbonded web of the desired fibers, and may also be a bonded-cardedweb. Layers of different materials that may have different fiber deniers can also be used. The various fabrics can be composed of natural fibers, synthetic fibers or combinations thereof. For example, the bodyside liner may comprise a spunbonded polypropylene.

The bodyside liner 124 can be composed of a substantially hydrophobic material, and the hydrophobic material may optionally be treated with a surfactant or otherwise processed to impart a desired level of wettability and hydrophilicity. Examples of suitable materials for the bodyside liner 124 include 0.3–0.5 osy (10–17 gsm) polypropylene spun bond web treated with a suitable wettability treatment, 0.3–0.5 osy (10–17 gsm) bonded carded web and 0.4–0.8 osy (14–27 gsm) thru air bonded carded web. The fabric can be surface treated with an operative amount of surfactant, such as about 0.28 percent Triton X-102 surfactant. The surfactant can be applied by any conventional means, such as spraying, printing, brush coating or the like.

In particular embodiments, the bodyside liner 124 is desirably extensible and capable of extending along with the outer cover 100 for desired fit of the diaper on the wearer. For example, the bodyside liner 124 can be composed of various extensible materials such as a necked fabric, a creped fabric, a micro-pleated fabric, perforated polymer films or the like, as well as combinations thereof. The fabrics may be woven or nonwoven materials, such as spunbond fabrics, that may be elastic or non-elastic. Examples of suitable manufacturing techniques and suitable necked nonwoven fabric materials for such an extensible top sheet 61 are described in U.S. Pat. No. 4,965,122 n entitled REVERSIBLY NECKED MATERIAL, by M. T. Morman which issued Oct. 23, 1990.

Desirably, the bodyside liner 124 is made from non-elastic neckable naterials for reduced cost and improved manufacturing efficiency. Suitable non-elastic neckable materials for such a configuration include nonwoven webs, woven materials and knitted materials. Such webs can include one or more fabric layers. Nonwoven fabrics or webs have been formed from many processes, for example, bonded carded web processes, meltblowing processes and spunbonding processes. The non-elastic neckable material is desirably formed from at least one member selected from fibers and filaments of inelastic polymers. Such polymers include polyesters, for example, polyethylene terephthalate, polyolefins, for example, polyethylene and polypropylene, polyarnides. These fibers or filaments are used alone or in a mixture of two or more thereof. Suitable fibers for forming the neckable material include natural and synthetic fibers as well as bicomponent, multi-component, and shaped polymer fibers. Many polyolefins are available for fiber production according to the present invention, for example, fiber forming polypropylenes include Exxon Chemical Company's Escorene PD 3445 polypropylene and Himont Chemical Company's PF-304. Polyethylenes such as Dow Chemical's ASPUN 6811A linear low density polyethylene, 2553 LLDPE and 25355 and 12350 high density polyethylene are also suitable polymers.

The neckable material may be necked to form the extensible bodyside liner 124 by conventional necking processes which typically vary the surface speed of the web to draw or neck the material. Such necking will allow the material to extend and retract in the transverse direction. As discussed above, such necked non-woven fabric materials typically are capable of being necked up to about 80 percent. For example, the extensible bodyside liner 124 may be necked from about 10 to about 80 percent, more desirably from about 20 to about 60 percent, and still more desirably from about 30 to about 50 percent for improved performance.

Figure 2:
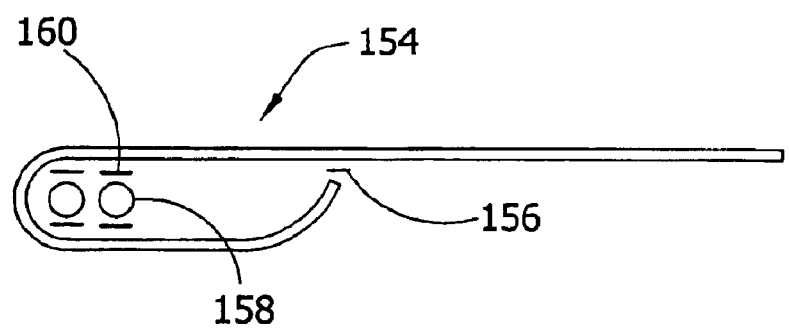
FIG. 2 is a cross sectional view of a containment flap.

Containment flaps 126 and 128 can be bonded to the outer cover, bodyside liner, or other intermediate layer. In the illustrated embodiment, the containment flaps 126 and 128 are bonded directly to the bodyside liner 124 with adhesive 146 and 148. A suitable adhesive for bonding the containment flaps to the bodyside liner includes the adhesive of the present invention. Typically, the containment flaps are first formed outside of the diaper manufacturing process and subsequently introduced into the manufacturing process for attachment to the bodyside liner. As illustrated in FIG. 2, the containment flap 154 is formed off-line by folding the construction material for the containment flap 154 over onto itself and securing it with adhesive 156, which may be the adhesive composition of the present invention. The folding over of the material traps a stretchable material 158, secured to the containment flap 154 with adhesive 160, within the containment flap. Adhesive 160 can be the adhesive composition of the present invention.

Referring again to FIG. 1, containment flaps 126 and 128 are configured to provide a barrier to the lateral flow of body exudates, and generally include a spunbond polypropylene and LYCRA or other stretchable material. Each containment flap typically has a free, or unattached end 142 and 144 free from connection with the bodyside liner 124 and other components of the diaper 101. Elastic strands 150 and 152 disposed within the containment flaps 126 and 128 adjacent the unattached ends thereof urge the flaps toward an upright, perpendicular configuration in at least the crotch region of the diaper 101 to form a seal against the wearer's body when the diaper is worn. The containment flaps 126 and 128 may extend longitudinally the entire length of the absorbent core 112 or they may extend only partially along the length of the absorbent core 112. When the containment flaps 126 and 128 are shorter in length than the absorbent core 112, the flaps can be selectively positioned anywhere between the side edges of the diaper and the crotch region of the diaper. In a particular aspect, the containment flaps 126 and 128 extend the entire length of the absorbent core 112 to better contain the body exudates. Containment flaps are generally well known to those skilled in the art. For example, suitable constructions and arrangements for containment flaps are described in U.S. Pat. No. 4,704,116 issued Nov. 3, 1987 to K. Enloe, the disclosure of which is hereby incorporated by reference in a manner consistent with the present document.

Referring now to FIG. 3, there is shown ears 138 and 140 (also commonly referred to as tabs or side panels) which are adhesively attached to diaper 101. The adhesive compositions, which attaches the ears to the diaper, may be the adhesive composition of the present invention. Typically, the ears 138 and 140 are separately formed and attached to the outer cover, to the bodyside liner, between the outer cover and the bodyside liner, or to other suitable components located in the ear attachment zone of the diaper. The ears 138 and 140 may be elastic or otherwise rendered elastomeric. For example, the ears 138 and 140 may be an elastomeric material such as a neck-bonded laminate (NBL) or stretch-bonded laminate (SBL) material. Methods of making such materials are well known to those skilled in the art and are described in U.S. Pat. No. 4,663,220 issued May 5, 1987 to Wisneski et al., U.S. Pat. No. 5,226,992 issued Jul. 13, 1993 to Mornan, and European Pat. Application No. EP 0 217 032 published on Apr. 8, 1987 in the names of Taylor et al., the disclosures of which are hereby incorporated by reference in a manner consistent with the present document. Examples of articles that include elasticized side panels and selectively configured fastener tabs are described in U.S. Pat. No. 5,496,298 issued Mar. 5, 1996 to Kuepper et al.; U.S. Pat. No. 5,540,796 to Fries; and U.S. Pat. No. 5,595,618 to Fries; the disclosures of which are also incorporated herein by reference in a manner consistent with the present document. Alternatively, the ears 138 and 140 may be formed integrally with a selected diaper component. For example, the ears 138 and 140 can be integrally formed with the inner or outer layer of the outer cover or may be integrally formed from with the bodyside liner.

Fastening components, such as hook fasteners 142 and 144 are typically employed on the ears 138 and 140 to secure the diaper 101 on the body of a child or other wearer by connecting the ears 138 and 140 to the pub patch (loop fastener) previously described. The hook fasteners 142 and 144 are adhesively bonded (not shown) to the ears 138 and 140. A suitable adhesive includes the adhesive compositions of the present invention. Alternatively, other fastening components (not shown), such as buttons, pins, snaps, adhesive tape fasteners, cohesives, mushroom-and-loop fasteners, or the like, may be employed. Desirably, the interconnection of the fastening components is selectively releasable and re-attachable. In the illustrated embodiment, the hook fasteners 142 and 144 are attached to and extend laterally out from the respective ears 138 and 140 at the back region of the diaper 101.

To provide improved fit and to help further reduce leakage of body exudates from the diaper 101, elastic components are typically incorporated into the diaper 101, particularly at the waist area and the leg areas. For example, as illustrated in FIG. 3, the diaper 101 has a waist elastic component 132 and leg elastics 134 and 136. The waist elastic 132 is configured to gather and shirr the end margins of the diaper 101 to provide a resilient, comfortable close fit around the waist of the wearer.

The leg elastic components are typically secured between the outer and inner layers of the outer cover, such as by being bonded to one or both layers by a laminate adhesive, such as the adhesive composition of the present invention. It should be understood, however, that the leg elastic components may be secured between the outer and inner layers of the outer cover by other methods.

Each elastic component generally comprises an elongate substrate, such as a sheet or ribbon, having threads or strands of elastic material secured to the substrate in generally parallel, spaced relationship with each other. As an example, one suitable elastic material from which the elastic strands may be constructed is a dry-spun coalesced multi-filament elastomeric thread sold under the trade name LYCRA and available from E.I. du Pont de Nemours (Wilmington, Del.). The elastic strands are desirably secured to the substrate while in a stretched condition such that the retractive forces of the elastic strands tend to gather the substrate. The substrate is in turn secured to the bodyside liner 124 which is turn is attached to the outer cover 100 with the substrate ungathered such that the retrative forces of the elastic strands gather the diaper at the leg openings to provide a snug fit around the wearer's leg. The various components of the diaper 101 are integrally assembled together using a suitable form of attachment, such as a combination of adhesives, sonic bonds, thermal bonds.

Examples of other diaper configurations suitable for use in connection with the instant application that may or may not include diaper components similar to those described previously are described in U.S. Pat. No. 4,798,603 issued Jan. 17, 1989, to Meyer et al.; U.S. Pat. No. 5,176,668 issued Jan. 5, 1993, to Bemardin; U.S. Pat. 5,176,672 issued Jan. 5, 1993, to Bruemmer et al.; U.S. Pat. No. 5,192,606 issued Mar. 9, 1993, to Proxmire et al., and U.S. Pat. No. 5,509,915 issued Apr. 23, 1996 to Hanson et al., the disclosures of which are hereby incorporated by reference in a manner consistent with this document.

To insure that the complex articles described above are assembled accurately, the physical properties of the materials used during the assembly process must be properly controlled. For instance, the failure to deliver a web of constant width of certain materials during the assembly process can affect the relative placement of components on the web, which can result in a defective product. As noted above, the liquid permeable outer layer 102, the body sideliner 124, the absorbent core 112, and various loop materials may each be part of a web, the width of which may effect their placement. Thus, by using a control scheme to control web width variability, the number of defective products produced during the assembly process can be reduced significantly.

Figure 4:
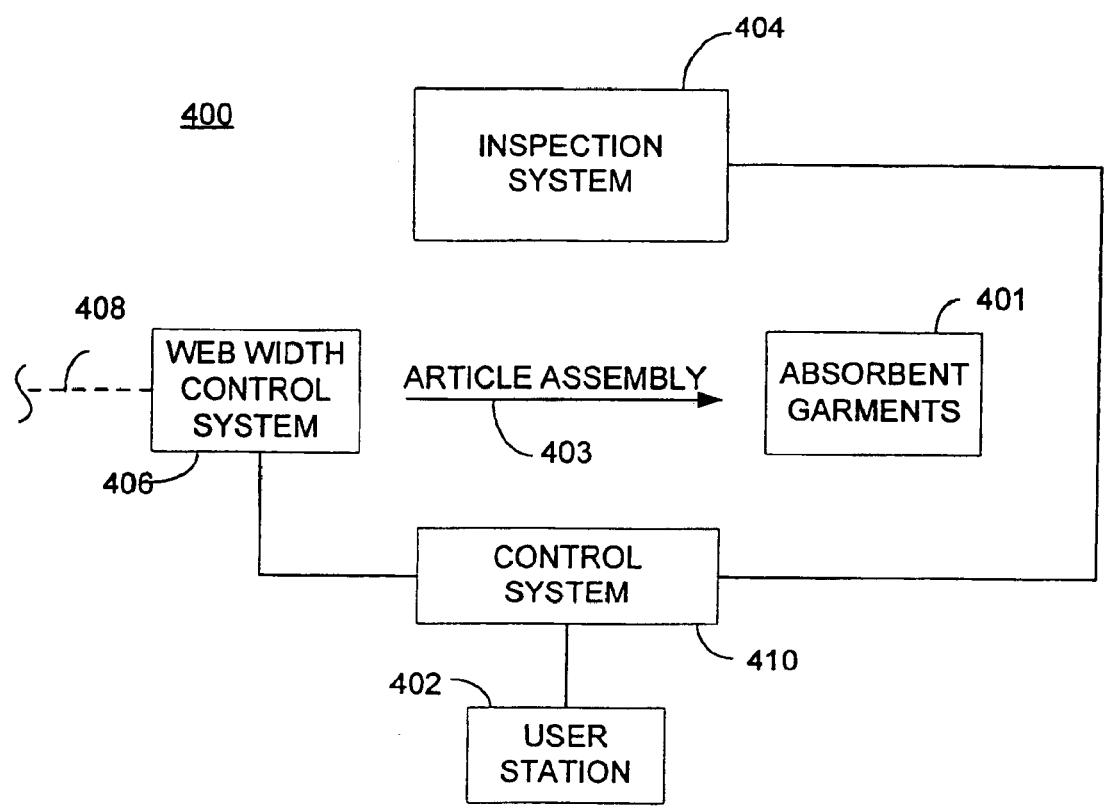
FIG. 4 is a block diagram illustrating a system for assembling pre-fastened articles such as absorbent garments.

Referring now to FIG. 4, a block diagram illustrates a system 400 for assembling pre-fastened articles such as absorbent garments 401. A user station 402 controls and monitors the assembly of absorbent garments 401 during an article assembly process, indicated by reference character 403. An inspection system 404 examines the assembled absorbent garments and detects and/or segregates defective absorbent garments. A web width control system 406 is responsive to web control information for maintaining a web material 408 delivered to the assembly process at a substantially constant width. A manufacturing control system 410 is responsive to the inspection system 404 and the user station 402. The web control system may employ control system 410, as illustrated, or it may have its own control (see FIG. 5). As can be seen by the system 400 illustrated in FIG. 4, the web control system 406 is located at the front end of the assembly process. Consequently, the web control system 406 affects the article assembly process, and, thus, can affect what is detected by the inspection system 404 and can affect the quality of the absorbent garments 401 produced by the system 400. Thus, an invention directed toward web width control during the article assembly process can be particularly instrumental in improving the quality of the absorbent garments 401 produced therefrom.

Existing systems and methods for controlling web width often involve monitoring and controlling web tension during manufacturing process. The present invention recognizes that the relationship between web tension and web width is not necessary a linear relationship. Although there are tension dependencies on width, controlling tension does not necessarily insure proper width. Thus, tension control often proves inadequate in controlling width variability.

Figure 5:
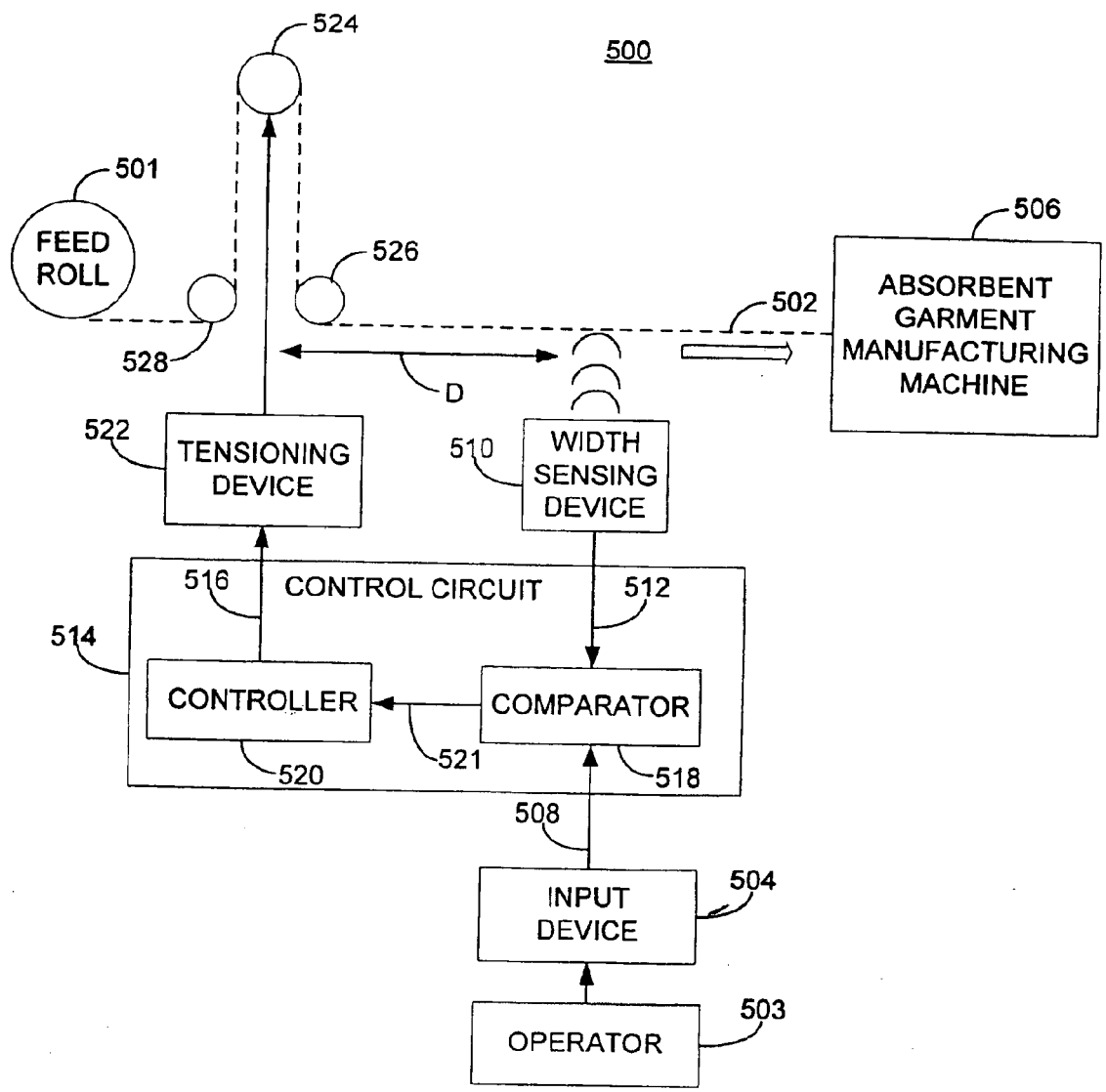
FIG. 5 is an exemplary block diagram illustrating the components of a system and method according to a preferred embodiment of the invention.

Referring now to FIG. 5, an exemplary block diagram illustrates a system 500 for controlling the width of a material supplied from a feed roll 501 to form a web 502 during a manufacturing process of an article, such as an absorbent garment manufactured by an absorbent garment manufacturing machine 506.

In one embodiment, an operator 503 uses an input device 504 to define a target width for the web 502. In this case, the input device 504 is a computer keyboard associated with a personal computer (PC) system that controls and monitors the tension of the web 502. In another embodiment (not shown), the target width information is automatically retrieved from a manufacturing database by the PC system that controls and monitors the tension of the web 502. The operator 503 using the input device 504 defines a desired target width of web 502 based on previous experiences or based on information the operator 503 retrieves from manufacturing reference manuals. For example, the operator 503 may refer to a manufacturing reference manual and determine a target width for the web 502 based on the particular type of absorbent garment which will be fabricated from the web 502. In this embodiment, target web widths can vary from less than one inch to greater than 24 inches. The operator 503 uses the input device 504 to enter a determined width of, for example, eleven inches (11"). In another embodiment, the operator 503 may use the input device 504 to define a target range for the width of the web 502 rather than a specific target width. For instance, the operator 503 uses a computer keyboard to enter keystrokes that define upper and lower limits for the width of web 502. Consequently, the upper and lower limits define a range of web widths that are acceptable during the manufacture of a particular absorbent garment (e.g. 11"–11.5"). Notably, a particular target width is a specific example of a target range. After the operator 503 enters the target width information, the input device 504 generates a reference signal 508. The reference signal 508 can be in a digital format or an analog format. For example, if the operator 503 uses a computer keyboard as the input device 504, the reference signal 508 will be generated in a digital format. Alternatively, if operator 503 uses a potentiometer as the input device 504, the reference signal 508 is generated in an analog format. In this latter embodiment, the reference signal 508 is a voltage having a magnitude corresponding to the target width of the web 502.

A width-sensing device 510 senses the width of the web 502 during the manufacturing process, and is configured to measure the width of web 502 using any system of measurement (e.g., metric or English). In one embodiment, the width-sensing device 510 is a linescan camera such as a Piranha P2-22-4096 manufactured by DALSA® Corporation which is configured to sense the width of the web 502 in millimeters (mm). In another embodiment, as described below in reference to FIG. 6, edge sensors are used for sensing the width of the web 502. In response to sensing the width of the web 502, the width-sensing device 510 generates a feedback signal 512, such as an analog voltage signal having a magnitude corresponding to the sensed width of the web 502. However, the feedback signal 512 can also be generated in a digital format. Although examples of the width sensing device 510 described herein include linescan cameras and edge sensors (See FIG. 6), the width-sensing device 510 is not limited to such embodiments and can include any width-sensing device 510 known to those skilled in the art.

A control circuit 514 is linked to the input device 504 and the width-sensing device 510 to receive the reference signal 508 and feedback signal 512, respectively. The control circuit 514 compares the reference signal 508 to the feedback signal 512 and generates a tensioning signal 516 corresponding to the difference between the signals. In one embodiment, the control circuit 514 includes a comparator 518 and a controller 520. The comparator 518 compares the reference signal 508 to the feedback signal 512 and generates a difference signal 521 (i.e., error signal). The controller 520 receives the difference signal 521 and generates the tensioning signal 516.

As described above, the tensioning signal 516 is a function of the comparison of reference signal 508 and feedback signal 512, and determines how the tension of the web 502 will be adjusted. For example, feedback signal 512 representing a sensed width which is lower than the desired target width represented by the reference signal 508 indicates that the width of the web 502 should be increased. In order to increase the width of web 502, the tensioning signal 516 must produce a decrease in the tension of the web 502. Alternatively, a feedback signal 512 indicating that the sensed width of web 502 is greater than the target width for web 502 means that the width of the web 502 should be decreased. In order to decrease the width of the web 502, the tensioning signal 516 must produce an increase in the tension of the web 502. Hence, the output of control circuit 514 applies the tensioning signal 516 to a tensioning device 522 to achieve the desired web width.

The tensioning device 522 responds to the tensioning signal 516 to change the tension of the web 502 and, thus, maintain the width of the web 502 within a target range or at the target width as indicated by operator 503 via the input device 504. In one embodiment, the tensioning device 522 is responsive to an applied voltage (i.e., tensioning signal 516) to actuate a dancer bar 524 that engages the web 502. For example, when the sensed width of web 502 is greater than the target width for web 502 the tensioning signal 516 applied to the tensioning device 522 actuates the dancer bar 524 such that the tension in the web 502 increases. The increased tension in the web 502 stretches the web 502 along its length and causes the width of web 502 to decrease to an amount that is within or at the target width. Alternatively, when the sensed width of web 502 is less than the target width for web 502, the tensioning signal 516 applied to the tensioning device 522 actuates the dancer bar 524 such that the tension in the web 502 decreases. The decreased tension in the web 502 reduces the stretch of the web 502 along its length and causes the width of web 502 to increase to an amount that is within or at the target width. In one embodiment, the dancer bar can be calibrated to apply from one (1) pound to ten (10) pounds of tensioning force to the web 502 to adjust the width of the web 502.

In another embodiment, the control circuit 514 controls the amount of force applied to web 502 by the dancer bar 524 by executing an algorithm that calculates the tensioning signal 516 as a function of a modulus of elasticity of the web 502 and Poisson's ratio for the web 502.

The modulus of a material is defined as the slope of the material's stress strain curve and can be calculated by the following equation:

$$E = \sigma/\epsilon; \quad (1)$$

where $\sigma$ is material stress, $\epsilon$ is material strain, and E is the modulus of elasticity.

Stress is the amount of load per unit area and can be calculated by the following equation:

$$\sigma = F/A; \quad (2)$$

where F is the force applied to the web, and A is the cross-sectional area of web.

Strain is defined as the amount of deflection per unit of an initial sample length and can be calculated by the following equation:

$$\epsilon = \Delta L/L_0; \quad (3)$$

where $\Delta L$ is the change in length of a sample length of the web 502, and $L_O$ is the initial sample length of the web 502.

Poisson's ratio is a number that characterizes the amount of change in one dimension due to a change in a perpendicular dimension and the mathematical definition of Poisson's ratio is:

$$\mu = (\Delta W/W_O)/(\Delta L/L_0); \quad (4)$$

where $\Delta W$ is the desired change in width of the web 502, $W_O$ is the initial width of the web 502, and $\mu$ is Poisson's ratio.

By combining equations 1 through 4, the following equation can be derived and used to calculate the amount of force to apply to the web to achieve the desired web width:

$$F = (AE\Delta W)/\mu(W_O). \quad (5)$$

In one embodiment, after the force is applied to the web 502 a separate control system external to the invention discussed herein is used to trim the speed of the feed roll 501. By trimming the speed of the feed roll 501, the tension of the web 502 is increased. As described above, an increase in the web tension results in a decrease in the force applied to the web 502. Thus, the separate control system is used to increase the tension in the web 502 until the force being applied is equal to an initial set point. In this case, the initial set point for the force is zero (0) and corresponds to a relaxed web width (i.e., $W_O$).

The tensioning device 522 is located along the web 502 upstream of a point along the web 502 at which the width of the web 502 is being sensed by the width-sensing device 510. A distance D between the location at which the tensioning device 522 engages the web 502 and the point at which the width of the web 502 is being sensed is greater than or equal to a minimum distance sufficient for rejecting or correcting transients in the width. Transients in web width can be caused by changes in tension implemented by the tensioning device 522 in response to the control circuit 514, roll wobble from unwind rolls with defective bearings, unwind splices, or adhesives applied to the web. To avoid these transients, it is often necessary to sense the web width at some minimum distance D downstream of the dancer. In one embodiment, the distance between the location at which the tensioning device 522 engages the web 502 and the point at which the width of the web 502 is being sensed is approximately 30 feet.

Although the tensioning device 522 is described herein as actuating a dancer bar 524 to adjust web tension, in an alternative embodiment (not shown) the tensioning device 522 can be used to adjust rotational speeds of nip rollers 526, 528 and thereby adjust the tension of the web 502.

Figure 6:
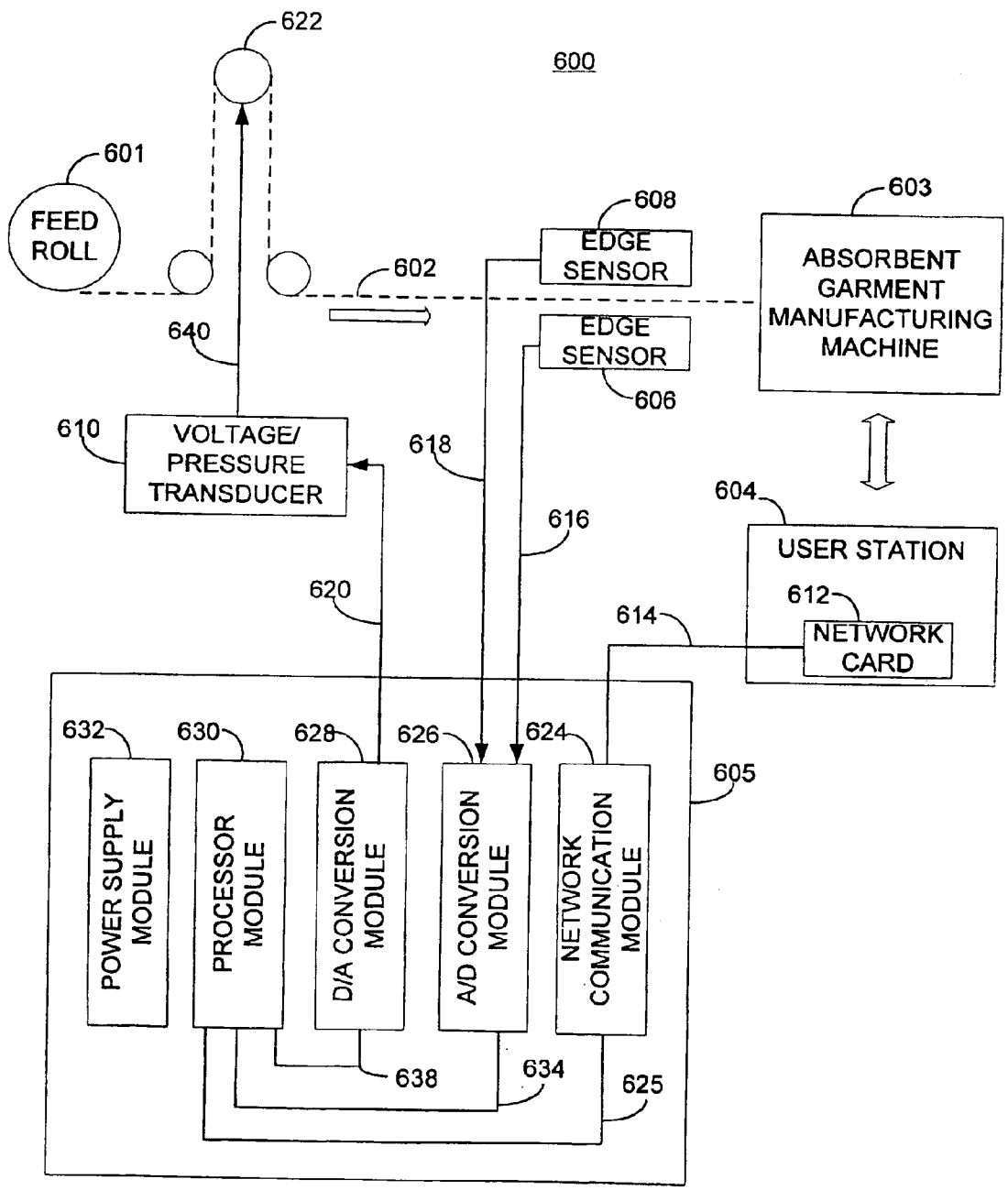
FIG. 6 is an exemplary block diagram illustrating a system including a controller for controlling the width of the web supplied to an absorbent garment manufacturing machine.

Referring now to FIG. 6, an exemplary block diagram illustrates a system 600 including a controller 605 to control the width of a web 602 supplied from a feed roll 601 to an absorbent garment-manufacturing machine 603 that manufactures absorbent garments.

A user station 604 controls and monitors the manufacture of absorbent garments on the absorbent garment-manufacturing machine 603. In one embodiment, the user station 604 is a personal computer (PC) system. As described in reference to FIG. 5, an operator can use a keyboard associated with the PC system to define a target width for the web 602 and generate a reference signal. In one embodiment, the user station 604 is associated with a computer network and includes a network-interface card 624 for communicating with other network devices. In such an embodiment, after the operator defines the target width for the web 602, the operator uses the user station 604 to communicate the reference signal to another network device such as the controller 605 via a link 614.

Edge sensors 606, 608 such as SE-38 sensors manufactured by FIFE® Corporation are used to generate analog feedback signals 616, 618, respectively. In one embodiment, edge sensor 606 detects a position of a first side edge of the web 602, and edge sensor 608 detects a position of a second side edge of the web 602. The edge sensors 606, 608 are positioned such that the detected position of the first side edge is located directly opposite the detected position of the second side edge. Thus, the analog feedback signals 616, 618 are representative of the position of the first side edge of the web 602 and the position of the second side edge of the web 602, and are used by the controller 605 to determine web width. Since the distance between the edge sensors 606, 608 is known or can be determined, the width of the web 602 can be calculated based on the positions of the edges relative to the sensors and the distance between the sensors.

Figure 6A:
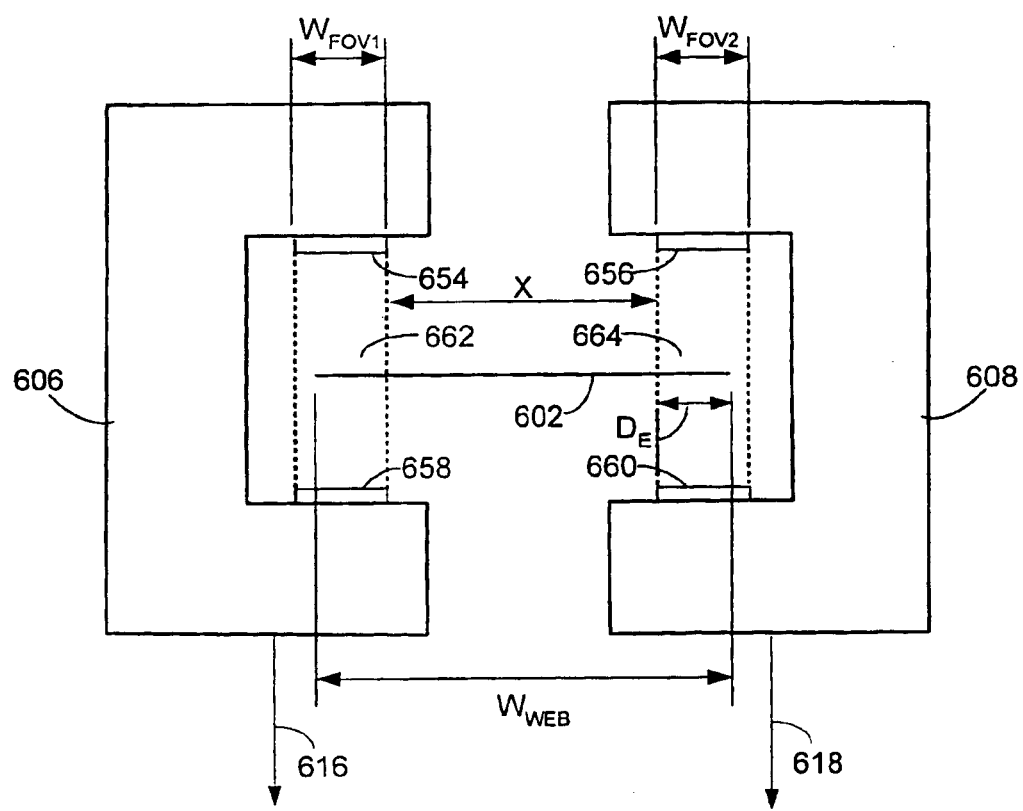
FIG. 6A is a cross sectional view illustrating an exemplary web width detection system.

Referring now to FIG. 6A, a cross section view shows an exemplary configuration of edge sensors 606, 608 such as SE-38 sensors manufactured by FIFE® Corporation for sensing the width of the web 602 as described in reference to FIG. 6. As described above, edge sensors 606, 608 are positioned such that the detected position of the first side edge is at a position across the web from and directly opposite to the detected position of the second side edge. In this embodiment, edge sensor 606 includes a transmitter 654 and corresponding receiver 658, and edge sensor 608 includes a transmitter 656 and a corresponding receiver 660. Transmitters 654, 656 emit light, and receivers 658, 660 detect light and generate analog signals 616, 618, respectively. Receivers 658, 660 detect light across a field of view (FOV) of the respective edge sensor as indicated by reference characters 662, 664. Analog signals 616, 618 generated by receivers 658, 660 are proportional to the amount of light detected by the respective receiver. In this case, the amount of light detected by receivers 658, 660 corresponds to a distance DE the web 602 extends into the FOV of the respective edge sensor. For example, each receiver can be calibrated such that the analog output has a magnitude of one (1) volt DC when the distance DE the web 602 extends into the FOV is greater than or equal to a width $W_{FOV}$ of the particular FOV. In other words, the analog output has a magnitude of one (1) volt DC when the web completely obstructs light from a particular transmitter from reaching the corresponding receiver. Further, each receiver can be calibrated such that the analog output has a magnitude of zero (0) volts DC when the web does not extends into the FOV (i.e., $D_E$=0). The width WFov of the FOV of each edge sensor is known, and the distance X between the FOV of edge sensor 606 and the FOV of second edge sensor 608 can be determined. Thus, the width of the web 602 can be calculated as a function of the FOV width, the distance between the FOV of edge sensor 606 and the FOV of edge sensor 608, and the analog output from edge sensors 606, 608. In one embodiment, the web width is calculated using the following equation:

$$W_{WEB}=X+V_1*(w_{FOV1}/1\text{VDC})+V_2*(w_{FOV2}/1VDC); \quad (6)$$

where $V_1$ is the analog output of edge sensor 606, $V_2$ is the analog output of edge sensor 608, $W_{FOV1}$ is the width of the FOV of edge sensor 606, $W_{FOV2}$ is the width of the FOV of edge sensor 608, and $W_{WEB}$ is the calculated width of the web 602.

Referring again to FIG. 6, analog signals 616, 618 are provided to an analog to digital conversion module 626 of controller 605, which converts the signals to corresponding digital signals which are provided to a processor module 630 of the controller 605. The processor module 630 calculates the sensed width of the web 602 and compares it to the target width as indicated to the network communication module 624 via the network card 612 and a link 614. Depending on the comparison, the processor module 630 provides a digital signal representative of the desired tension of the web 602. For example, if the sensed width is greater than the target width, the tension of the web 602 needs to be increased so that digital signal would have an increased digital value. As another example, if the sensed width is less than the target width, the tension of the web 602 needs to be decreased so that digital signal would have a decreased digital value. The digital signal is provided via 638 to a digital to analog conversion module 628 which converts the digital signal into a corresponding analog signal provided as a tensioning signal 620.

In this embodiment, a voltage to pressure transducer 610 receives the tensioning signal 620 from the controller 605. The voltage to pressure transducer 610 is used to increase or decrease an air pressure 640 supplied to a pneumatically controlled dancer bar 622. For example, when the width of web 602 is determined to be greater than the target width for web 602, the tensioning signal 620 applied to the voltage to pressure transducer 610 increases the air pressure 640 to raise the dancer bar 622 and increase tension in the web 602. The increased tension in the web 602 causes the width of web 602 to decrease to an amount that is within or at the target width. Alternatively, when the width of web 602 is determined to be less than the target width for web 602, the tensioning signal 620 applied to the voltage to pressure transducer 610 decreases the air pressure 640 lower the dancer bar 622 and decrease tension in the web 602. The decreased tension in the web 602 causes the width of web 602 to increase to an amount that is within or at the target width. In one embodiment, a preset air pressure is supplied to the pneumatically controlled dancer bar 622 such that the tensioning signal 620 supplied to the voltage to pressure transducer 610 increases or decreases the air pressure from the preset air pressure.

In one embodiment, the controller 605 is a programmable logic controller (PLC) such as an RELIANCE® AUTOMAX® Controller manufactured by Rockwell Automation that can be programmed to control a process or machine operation. In such an embodiment, the controller 605 contains areas or slots where input/output (I/O) modules (i.e., racks) can be connected directly to the controller 605. The I/O modules serve as the interface through which input and output devices are connected. In this instance, the user station 604 and edges sensors 606, 608 are input devices and the voltage to pressure transducer 610 is an output device. In this embodiment, the I/O modules include a network communications module 624, a digital to analog conversion module 626, an analog to digital conversion module 628, a processor module 630, and a power supply module 632. The network communications module 624 allows the controller 605 to communicate with other network devices and with other I/O modules in the controller 605. The digital to analog conversion module 626 converts signals from a digital format to an analog format. The analog to digital conversion module 628 converts signals from an analog format to a digital format. The processor module 630 receives digital input, and is programmable for generating a digital output as function the digital input. A power supply module 632 regulates and supplies power to the modules of the controller 605.

In operation, the operator uses the user station 604 to define a target web width. The user station 604 generates a digital reference signal representative of the target web width which is transferred to the network communications module 624 via the network card 612 and link 614. The network communications module 624 communicates the digital reference signal to the processor module 630 via a link 625. Edge sensors 606, 608 detect the positions of opposite side edges of the web 602 and produce analog feedback signals 616, 618 that are representative of the detected positions. The analog feedback signals 616, 618 are provided to the analog to digital conversion module 628 of the controller 605. The analog to digital conversion module 628 converts the analog feedback signals 616, 618 to digital feedback signals and provides the digital feedback signals to the processor module 630 via a link 634. The processor module 630 compares the sensed web width, as indicated digital feedback signals, to the desired width as indicated by digital reference signal and generates a digital tensioning signal as a function of the difference. The processor module 630 provides the digital tensioning signal to the digital to analog conversion module 628 via link 638. Links 625, 634, and 638 may be a bus. The digital to analog conversion module 626 converts the digital tensioning signal to an analog tensioning signal 620. The analog tensioning signal 620 is applied to the voltage-to-pressure transducer 610 to vary the air pressure 640. The air pressure 640 applies a pneumatically controlled dancer bar 622 to the web to adjust the position of the dancer bar 622 and to vary the tension in the web 602. For example, the position of the dancer bar 622 is lowered to decrease the tension of the web 602 when the comparison between the digital reference signals and digital feedback signal indicates the web width is less than the target width. Alternatively, the position of the dancer bar 622 is raised to increase the tension of the web 602 when the comparison between the digital reference signals and digital feedback signal indicates the web width is greater than the target width.

In one embodiment, the user station 604 contains control software such as AUTOMAX® Programming Executive available from Rockwell Automation, which can be used for configuring the processor module 630 to execute an algorithm that employs equation 5 to generate the digital tension signal.

In another embodiment (not shown), a servo is linked to the controller 605 for receiving a pulse width modulation (PWM) signal. The servo includes a geared motor which is mechanically linked to the dancer bar 622 such that when the servo drives the motor, it rotates the gears which causes the dancer bar to raise or to lower. In this case, the processor module 630 compares the sensed web width, as indicated by digital feedback signals, to the desired width as indicated by a digital reference signal and generates the PWM signal as a function of the difference. The servo is responsive to the PWM signal and turns the geared motor to raise or to lower the dancer bar 622. For example, the position of the dancer bar 622 is lowered to decrease the tension of the web 602 when the comparison between the digital reference signal and digital feedback signals indicates the web width is less than the target width. Alternatively, the position of the dancer bar 622 is raised to increase the tension of the web 602 when the comparison between the digital reference signals and digital feedback signal indicates the web width is greater than the target width.

Figure 7:
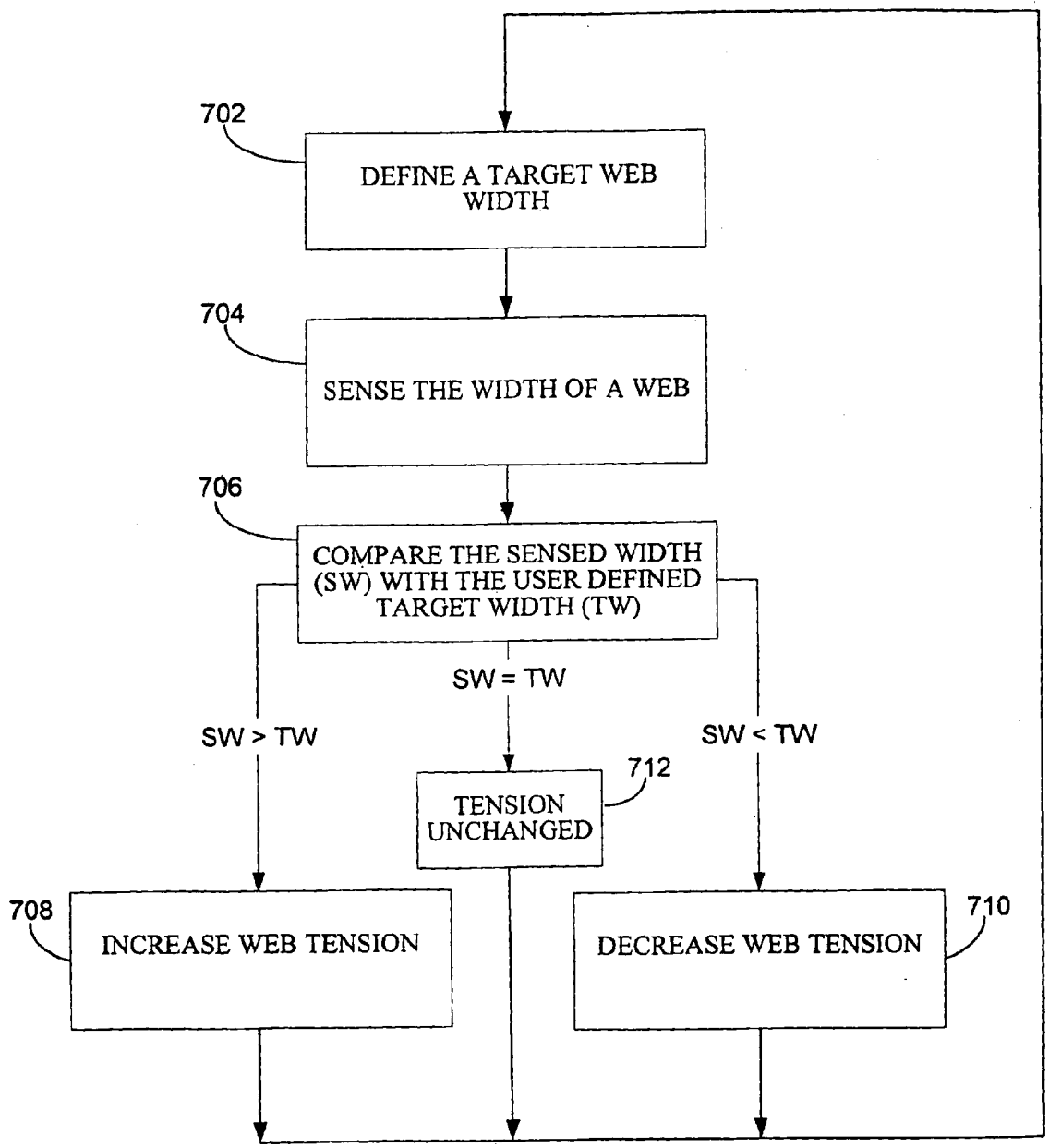
FIG. 7 is an exemplary flow chart illustrating a method for managing a manufacturing processing operation according to one preferred embodiment of the invention.

Referring now to FIG. 7, an exemplary flow chart illustrates a method for managing a manufacturing processing operation according to exemplary embodiment described in reference to FIG. 5. At step 702, operator 503 uses input device 504 to define the target web width and generate reference signal 508 that is representative of the target web width as defined by operator 503 via input device 504. At step 704, width-sensing device 510 senses the width of web 502 being supplied during the manufacturing process and generates feedback signal 512 that is representative of the sensed web width. At step 706, reference signal 508 and feedback signal 512 are compared and a tensioning signal 516 is generated as a function of the difference. If feedback 512 signal indicates the sensed width of web 502 is greater than the target width, the web tension is increased at step 708. If the feedback signal 516 indicates that the sensed width of web 502 is less than the target width, the web tension is decreased at step 710. If step 706 determines that the sensed width of the web 502 is equal to the target width or range, the tension remains unchanged as indicated by step 712. Throughout the manufacturing process, step 706 and alternative steps 708, 710 or 712 are repeated to maintain the web width at or within the target web width or range. Although FIG. 7 refers to a target width, a target range is also contemplated. In this case, a target width is a specific example of a target range.

When introducing elements of the present invention or the embodiment(s) thereof, the articles "a," "an," "the," and "said" are intended to mean that there are one or more of the elements. The terms "comprising," "including," and "having" are intended to be inclusive and mean that there may be additional elements other than the listed elements.

In view of the above, it will be seen that the several objects of the invention are achieved and other advantageous results attained.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A system for controlling a web material traveling along a path for use during an absorbent garment manufacturing process, comprising:
    an input device responsive to operator information for indicating a target width range;
    a width sensor sensing a width of the web material;
    a tensioning device for controlling a tension of the web material in response to a tensioning signal; and
    a control circuit linked to the input device and the width sensor, wherein said control circuit is responsive to the input device and responsive to the width sensor for providing the tensioning signal for controlling the tensioning device to maintain the width of the web within the target width range as indicated by the input device.

2. The system of claim 1, further comprising an absorbent garment manufacturing machine for receiving the web and for producing absorbent garments therefrom, and a feed roll for supplying the web.

3. The system of claim 1, wherein the width sensor is a linescan camera configured to sense the width of the web material.

4. The system of claim 1, wherein the tensioning device engages the web at a location along the path which is upstream of a point along the path at which the width sensor senses the width of the web material, and wherein a distance between the location at which the tensioning device engages the web and the point being sensed by the width sensor is greater than or equal to a minimum distance such that transients in the web width at the point being sensed by the width sensor are minimized.

5. The system of claim 1, wherein the width sensor generates a feedback signal that is representative of the width of the web material, and wherein the input device generates a reference signal that is representative of a particular target width for said web material, wherein the control circuit compares the feedback signal and the reference signal and provides to the tensioning device as the tensioning signal a signal corresponding to the difference, and wherein the tensioning device adjusts the tension of the web in response to the tensioning signal.

6. The system of claim 5, wherein the control circuit comprises a comparator for comparing the feedback signal and the reference signal, and a controller responsive to the comparator for generating the tensioning signal corresponding to the difference.

7. The system of claim 1, wherein the input device is responsive to operator information for indicating a specific target width, and wherein the control circuit is responsive to the input device and responsive to the width sensor for providing the tensioning signal for controlling the tensioning device to maintain the width of the web at the specific target width as indicated by the input device.

8. The system of claim 1, wherein the width sensor comprises a first edge sensor for detecting a first side edge of the web, a second edge sensor for detecting a second side edge of the web, wherein the detected first side edge is transversely aligned with the detected second side edge, and wherein the width sensor generates a signal representative of the distance between the detected first side edge and the detected second side edge.

9. The system of claim 1, wherein the control circuit actuates the tensioning device to increase the tension of the web material when the sensed width of the web material is greater than the target width range, and wherein the control circuit actuates the tensioning device to decrease the tension of the web when the sensed width of web material is leas than the target web width range.

10. The system of claim 1, wherein the tensioning device comprises a voltage to pressure transducer linked to a dancer bar.

11. A system for controlling a web material traveling along a path for use during an absorbent garment manufacturing process comprising:
 a user station responsive to operator information for generating a reference signal indicating a target width range;
 a width sensor for sensing a width of the web material and generating a feedback signal;
 a tensioning device for adjusting a tension of the web material in response to a tensioning signal; and
 a controller linked to the user station and to the width sensor for receiving the reference signal and the feedback signal, the controller generating the tensioning signal as a function of the difference between the received reference signal and received feedback signal, and wherein the generated tensioning signal is provided to the tensioning device to adjust the tension of the web material to maintain the width of the web within the target width range.

12. The system of claim 11, wherein the user station is linked with an absorbent garment manufacturing machine receiving the web and producing absorbent garments therefrom.

13. The system of claim 11, wherein the tensioning device engages the web at a location along the path which is upstream of a point along the path at which the width sensor senses the width of the web material, and wherein a distance between the location at which the tensioning device engages the web and the point being sensed by the width sensor is greater than or equal to a minimum distance such that transients in the web width at the point being sensed by the width sensor are minimized.

14. The system of claim 11, wherein the width sensor generates a feedback signal that is representative of the width of the web material, and wherein the user station generates a reference signal that is representative of a particular target width for said web material input by the user via the input device, wherein the control circuit compares the feedback signal and the reference signal and provides to the tensioning device as the tensioning signal a signal corresponding to the difference, and wherein the tensioning device adjusts the tension of the web in response to the tensioning signal.

15. The system of claim 11, wherein the width sensor comprises a first edge sensor for detecting a position of a first side edge of the web, a second edge sensor for detecting a position of a second side edge of the web, wherein the detected position of the first side edge is transversely aligned with the detected position of the second side edge, wherein the first edge sensor generates a first analog feedback signal representative of the detected position of the first side edge and the second edge sensor generates a second analog feedback signal representative of the detected position of the second side edge, and wherein the controller is responsive to the first analog feedback signal and to the second analog feedback signal for determining the width of the web.

16. The system of claim 15, wherein the controller comprises an analog to digital converter for converting the analog feedback signal representative of the detected position of the first side edge of the web and the analog feedback signal representative of the detected position of the second side edge of the web to digital feedback signals, wherein the controller comprises a processor for comparing the digital feedback signals and a digital reference signal input by the user via the user station and generating a digital tensioning signal as a function of the difference, and wherein the controller comprises a digital-to-analog converter for converting the digital tensioning signal to an analog tensioning signal provided to the tensioning device as the tensioning signal.

17. The system of claim 16, wherein the tensioning device comprises a voltage to pressure transducer linked to a dancer bar, and wherein the voltage to pressure transducer is responsive to the analog tensioning signal for actuating the dancer bar and adjusting the tension of the web.

18. A system for use with a manufacturing process for manufacturing an absorbent garment from a web material traveling along a path comprising:
 [n] user station responsive to operator information for indicating a target width range;

a width sensor sensing a width of the web material;

a tensioning device for controlling a tension of the web material in response to a tensioning signal;

an inspection system for monitoring the manufacturing process; and a control system linked to the user station, to the inspection system, and to the width sensor, wherein said control system is responsive to the user station, responsive to the inspection system and responsive to the width sensor for controlling the manufacturing process and for providing the tensioning signal for controlling the tensioning device to maintain the width of the web within the target width range as indicated by the user station.

19. The system of claim 18, wherein the width sensor generates a feedback signal that is representative of the width of the web material, and wherein the user station generates a reference signal that is representative of a particular target width for said web material, wherein the control system compares the feedback signal and the reference signal and provides to the tensioning device as the tensioning signal a signal corresponding to the difference, and wherein the tensioning device adjusts the tension of the web in response to the tensioning signal.

20. The system of claim 19, wherein the control system comprises a comparator for comparing the feedback signal and the reference signal, and a control system responsive to the comparator for generating the tensioning signal corresponding to the difference.

21. The system of claim 18, wherein the user station is responsive to operator information for indicating a specific target width, and wherein the control system is responsive to the user station and responsive to the width sensor for providing the tensioning signal for controlling the tensioning device to maintain the width of the web at the specific target width as indicated by the user station.

22. The system of claim 18, wherein the control system actuates the tensioning device to increase the tension of the web material when the sensed width of the web material is greater than the target width range, and wherein the control system actuates the tensioning device to decrease the tension of the web when the sensed width of web material is less than the target web width range.

23. The system of claim 18, wherein the width sensor comprises a first edge sensor for detecting a position of a first side edge of the web, a second edge sensor for detecting a position of a second side edge of the web, wherein the detected position of the first side edge is transversely aligned with the detected position of the second side edge, wherein the first edge sensor generates a first analog feedback signal representative of the detected position of the first side edge and the second edge sensor generates a second analog feedback signal representative of the detected position of the second side edge, and wherein the control system is responsive to the first analog feedback signal and to the second analog feedback signal for determining the width of the web.

24. The system of claim 23, wherein the control system comprises an analog to digital converter for converting the analog feedback signal representative of the detected position of the first aide edge of the web and the analog feedback signal representative of the detected position of the second side edge of the web to digital feedback signals, wherein the control system comprises a processor for comparing the digital feedback signals and a digital reference signal input by the user via the user station and generating a digital tensioning signal as a function of the difference, and wherein the control system comprises a digital-to-analog converter for converting the digital tensioning signal to an analog tensioning signal provided to the tensioning device as the tensioning signal.

* * * * *